US011229467B2

(12) United States Patent
Dupuy et al.

(10) Patent No.: US 11,229,467 B2
(45) Date of Patent: Jan. 25, 2022

(54) VALVE FOR PREFILLED BONE CEMENT MIXING SYSTEM

(71) Applicant: ZIMMER GMBH, Winterthur (CH)

(72) Inventors: Alexis Dupuy, Sancourt (FR); Sebastien Chaligne, Brette les Pins (FR); Lenaic Giffard, Valence (FR)

(73) Assignee: Zimmer GmbH, Winterthur (CH)

( * ) Notice: Subject to any disclaimer, the term of this patent is extended or adjusted under 35 U.S.C. 154(b) by 216 days.

(21) Appl. No.: 16/375,265

(22) Filed: Apr. 4, 2019

(65) Prior Publication Data

US 2019/0314075 A1 Oct. 17, 2019

Related U.S. Application Data

(60) Provisional application No. 62/656,192, filed on Apr. 11, 2018.

(51) Int. Cl.

| | |
|---|---|
| ***A61B 17/88*** | (2006.01) |
| ***A61F 2/28*** | (2006.01) |
| ***B01F 15/02*** | (2006.01) |

(52) U.S. Cl.

CPC ...... *A61B 17/8833* (2013.01); *A61B 17/8827* (2013.01); *A61F 2/2846* (2013.01);

(Continued)

(58) Field of Classification Search

CPC ............ A61B 17/8805; A61B 17/8808; A61B 17/8811; A61B 17/8816; A61B 17/8819; A61B 17/8822; A61B 17/8825; A61B 17/8827; A61B 17/8833; A61B 17/8836; A61B 2017/8813; A61B 2017/883; A61B 2017/8838; A61M 39/24;

(Continued)

(56) References Cited

U.S. PATENT DOCUMENTS

| | | | |
|---|---|---|---|
| 4,827,973 | A | 5/1989 | Boehmer |
| 4,861,335 | A | 8/1989 | Reynolds |

(Continued)

FOREIGN PATENT DOCUMENTS

| | | | |
|---|---|---|---|
| CN | 1972648 | A | 5/2007 |
| CN | 101505860 | A | 8/2009 |

(Continued)

OTHER PUBLICATIONS

"U.S. Appl. No. 15/660,177, Examiner Interview Summary dated May 4, 2020", 3 pgs.

(Continued)

*Primary Examiner* — Eric S Gibson

(74) *Attorney, Agent, or Firm* — Schwegman Lundberg & Woessner, P.A.

(57) ABSTRACT

According to one example, a valve for an apparatus configured to mix bone cement is disclosed. The valve can include a base defining a first portion of a passage. The passage can be configured to allow a component of the bone cement through the valve. The valve can include a projection extending from the base to a base opposing end and forming a second portion of the passage that communicates with the first portion. The projection can have a frustoconically shaped surface that comprises one of an outer surface or an inner surface that forms a part of the second portion of the passage.

22 Claims, 12 Drawing Sheets

(52) U.S. Cl.
CPC .. *B01F 15/0278* (2013.01); *A61B 2017/8838* (2013.01); *A61L 2430/38* (2013.01); *B01F 2215/0029* (2013.01)

(58) Field of Classification Search
CPC .... A61M 2039/2406; A61M 2039/242; A61M 2039/2426; A61M 2039/2433; F16K 15/147; F16K 17/28
See application file for complete search history.

(56) References Cited

U.S. PATENT DOCUMENTS

| | | | | |
|---|---|---|---|---|
| 5,067,948 | A | 11/1991 | Haber et al. | |
| 5,261,459 | A * | 11/1993 | Atkinson | A61M 39/24 137/846 |
| 7,018,089 | B2 | 3/2006 | Wenz et al. | |
| 10,905,485 | B2 | 2/2021 | Giffard et al. | |
| 2006/0184137 | A1 | 8/2006 | Reynolds | |
| 2006/0274601 | A1 | 12/2006 | Seaton, Jr. | |
| 2011/0203691 | A1* | 8/2011 | Gerlich | F16K 15/148 137/856 |
| 2012/0277688 | A1* | 11/2012 | Rogier | A61M 39/045 604/247 |
| 2014/0192611 | A1 | 7/2014 | Sasaki et al. | |
| 2014/0251694 | A1* | 9/2014 | Crane | F16K 15/147 175/73 |
| 2015/0032063 | A1* | 1/2015 | Thorne | F16K 15/147 604/207 |
| 2015/0103616 | A1 | 4/2015 | Giffard et al. | |
| 2015/0202424 | A1* | 7/2015 | Harton | A61M 39/22 604/248 |
| 2015/0308582 | A1* | 10/2015 | Basham | F16K 24/04 137/388 |
| 2016/0030730 | A1* | 2/2016 | Mosier | A61M 39/225 604/508 |
| 2016/0038209 | A1 | 2/2016 | Grebius et al. | |
| 2016/0045242 | A1 | 2/2016 | Bielenstein et al. | |
| 2016/0312910 | A1* | 10/2016 | Stanton | A61M 39/26 |
| 2017/0120037 | A1 | 5/2017 | Thorne | |
| 2017/0198826 | A1* | 7/2017 | Chen | F16K 17/168 |
| 2018/0028247 | A1 | 2/2018 | Giffard et al. | |
| 2018/0128392 | A1* | 5/2018 | Wang | F16K 17/30 |
| 2019/0314075 | A1* | 10/2019 | Dupuy | A61B 17/8827 |
| 2020/0309273 | A1* | 10/2020 | Georgelos | B65D 47/2031 |

FOREIGN PATENT DOCUMENTS

| | | | |
|---|---|---|---|
| CN | 105268359 | A | 1/2016 |
| CN | 106321916 | A | 1/2017 |
| CN | 107289156 | A | 10/2017 |
| CN | 109789382 | A | 5/2019 |
| DE | 4425218 | A1 | 1/1996 |
| DE | 10302488 | A1 | 1/2005 |
| EP | 0727531 | A1 | 8/1996 |
| JP | 09510659 | A | 10/1997 |
| JP | 2001104482 | A | 4/2001 |
| JP | 2019524261 | A | 9/2019 |
| WO | WO-9607472 | A1 | 3/1996 |
| WO | WO-2004026377 | A1 | 4/2004 |
| WO | WO-2006118748 | A1 | 11/2006 |
| WO | WO-2008022481 | A1 | 2/2008 |
| WO | WO-2018019967 | A2 | 2/2018 |

OTHER PUBLICATIONS

"U.S. Appl. No. 15/660,177, Final Office Action dated Mar. 9, 2020", 8 pgs.
"U.S. Appl. No. 15/660,177, Non Final Office Action dated Aug. 15, 2019", 9 pgs.
"U.S. Appl. No. 15/660,177, Notice of Allowance dated Sep. 29, 2020", 9 pgs.
"U.S. Appl. No. 15/660,177, Response filed Jun. 9, 2020 to Final Office Action dated Mar. 9, 2020", 10 pgs.
"U.S. Appl. No. 15/660,177, Response filed Jul. 10, 2019 to Restriction Requirement dated May 23, 2019", 7 pgs.
"U.S. Appl. No. 15/660,177, Response filed Nov. 13, 2019 to Non Final Office Action dated Aug. 15, 2019", 11 pgs.
"U.S. Appl. No. 15/660,177, Restriction Requirement dated May 23, 2019", 7 pgs.
"Chinese Application Serial No. 201780054934.5, Office Action dated Feb. 19, 2021", w/English Translation, 20 pgs.
"European Application Serial No. 17748451.6, Communication Pursuant to Article 94(3) EPC dated Apr. 3, 2020", 5 pgs.
"European Application Serial No. 17748451.6, Response filed Aug. 13, 2020 to Communication Pursuant to Article 94(3) EPC dated Apr. 3, 2020", 12 pages.
"European Application Serial No. 17748451.6, Response to Communication pursuant to Rules 161(1) and 162 EPC filed Sep. 23, 2019", 17 pgs.
"European Application Serial No. 19168224.4, Extended European Search Report dated Mar. 12, 2020", 9 pgs.
"European Application Serial No. 19168224.4, Response filed Oct. 15, 2020 to Extended European Search Report dated Mar. 12, 2020", 10 pgs.
"Japanese Application Serial No. 2019-504038, Notification of Reasons for Refusal dated Mar. 10, 2020", (W/ English Translation), 9 pgs.
"Japanese Application Serial No. 2019-504038, Response filed Jun. 10, 2020 to Notification of Reasons for Refusal dated Mar. 10, 2020", (W/ English Translation of Claims), 18 pgs.
"International Application Serial No. PCT/EP2017/069093, International Preliminary Report on Patentability dated Feb. 7, 2019", 14 pgs.
"International Application Serial No. PCT/EP2017/069093, International Search Report dated Jan. 29, 2018", 7 pgs.
"International Application Serial No. PCT/EP2017/069093, Invitation to Pay Additional Fees and Partial Search Report dated Nov. 28, 2017", 15 pgs.
"International Application Serial No. PCT/EP2017/069093, Written Opinion dated Jan. 29, 2018", 12 pgs.
"Chinese Application Serial No. 201780054934.5, Office Action dated Jul. 20, 2021", (W/English Translation), 5 pgs.
"Chinese Application Serial No. 201780054934.5, Response filed May 20, 2021 to Office Action dated Feb. 19, 2021", (W/ English Claims), 13 pgs.

* cited by examiner

VALVE FOR PREFILLED BONE CEMENT MIXING SYSTEM

CLAIM OF PRIORITY

This application claims the benefit of U.S. Provisional Patent Application Ser. No. 62/656,192, filed on Apr. 11, 2018, the benefit of priority of which is claimed hereby, and which is incorporated by reference herein in its entirety.

FIELD OF THE DISCLOSURE

The present disclosure relates to surgical implant systems, including related systems including values and other apparatuses and used for mixing bone cement.

BACKGROUND

Bone cement is a substance that can be used by surgeons to anchor or help anchor components of an implant or fuse bone. For example, bone cement can be used to secure components, such as knee components, hip components, etc. to existing bone during joint replacement procedures. Bone cement also can be used to fuse bones, such as vertebra.

SUMMARY

According to one example, a valve for an apparatus configured to mix bone cement is disclosed. The valve can include a base defining a first portion of a passage. The passage can be configured to allow a component of the bone cement through the valve. The valve can include a projection extending from the base to a base opposing end and forming a second portion of the passage that communicates with the first portion. The projection can have a frustoconically shaped surface that comprises one of an outer surface or an inner surface that forms a part of the second portion of the passage.

Other examples of valves and apparatuses and systems configured to mix bone cement are provided herein.

BRIEF DESCRIPTION OF THE FIGURES

The above-mentioned and other features and advantages of this disclosure, and the manner of attaining them, will become more apparent and the disclosure itself will be better understood by reference to the following description of embodiments taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure any manner.

DETAILED DESCRIPTION

Figure 1A:
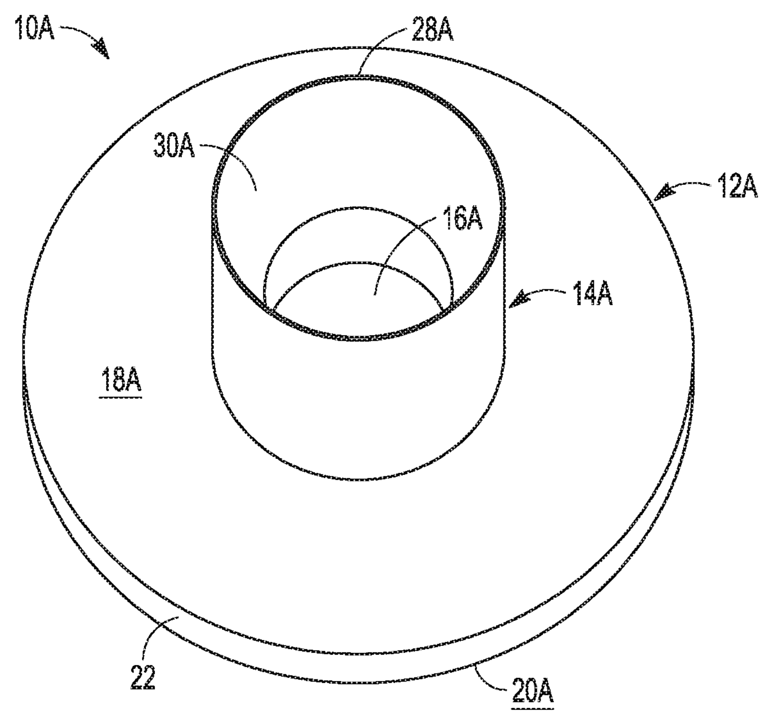
FIGS. 1A-1D shows a valve according to one example of the present disclosure.

As used herein, the following directional definitions apply. Anterior and posterior mean nearer the front or nearer the rear of the body, respectively, proximal and distal mean nearer to or further from the root of a structure, respectively, and medial and lateral mean nearer the sagittal plane or further from the sagittal plane, respectively. The sagittal plane is an imaginary vertical plane through the middle of the body that divides the body into right and left halves.

Bone cement can be a multicomponent substance and each of the components can be mixed at a time of use. For example, during a hip arthroplasty a surgeon can mix bone cement components as needed to secure implant components, such as a femoral component or an acetabular component. The bone cement components can be contained in a single apparatus or system. For example, a first component, such as a powder or other solid bone cement component, can be stored in a mixing chamber and a second component, such as a liquid or monomer, can be stored in a pouch.

To mix the first component and the second component of the bone cement, a base, which can include the pouch, can be inserted into a connecting cylinder of the system or apparatus. Upon making a relative movement between the base and the connecting cylinder, one or more cannulas can puncture the pouch. A vacuum created in the mixing chamber prior to making the relative movement between the mixing chamber and the connecting cylinder can cause the second component to flow into the mixing chamber upon puncturing of the pouch.

A piston can be located within the mixing chamber. The base can define a conduit sized to receive the cannula such that the second component can pass through the one or more cannulas and the conduit into the mixing chamber upon puncturing of the pouch by the one or more cannulas. A valve, such as a further described below, can be in fluid communication with the conduit and can seal the connection between the mixing chamber and the connecting cylinder conduit, in order the allow the second component free flowing into the mixing chamber due to pressure gradient.

After the first and second bone cement components have entered the mixing chamber and have been mixed, the base or, the connecting cylinder including the base, can be removed and the valve can seal the first and second bone cement components in the mixing chamber. The piston can pass from the first position to a second position thanks to the sealing by the valve and an air pressure difference in the mixing chamber relative to other communicating components of the assembly and/or the environment. To deliver the bone cement, the cap or handle can be removed from the mixing chamber and the mixing chamber can be connected to an applicator for delivery by the surgeon.

Achieving a desired seal via the valve can be important at several steps in the above described process. For example, it can be desirable for the valve to be configured to achieve the seal for the duration of a shelf life storage of the apparatus or system prior to use in mixing described above. Additionally, the valve creates and maintains the seal to prevent air leakage into the mixing chamber during collection and mixing of the bone cement. Optionally, such sealing can be maintained during delivery of the bone cement from the mixing chamber such as via the applicator. However, in some cases, the seal may no longer be applied once delivery has begun. Also, it can be desirable for the valve to be configured to ensure good assembly with the base, conduit, piston and/or cannula to achieve the seal.

After extensive experiment, the present inventors determined that to create the desired seal, the valve can have a construction that (1) minimizes a thickness of the valve at the extremity (.i.e. at and adjacent a tip of the valve), (2) provides for a frustoconically shaped surface, and/or (3) provides for a cylindrical shape at the extremity in an un-collapsed valve condition. Each of these features will be discussed in further detail below.

The seal can be constructed of a chemically stable material such as an elastomeric material (e.g., silicone, polyacrylate, ethylene propylene diene monomer ("EPDM"), fluoroelastomer ("FKM"), and/or nitrile ("NBR")). However, the present inventors conducted extensive testing, the results of which determined that silicone can be a most desired material for the valve as it can be capable of achieving very thin thickness(es), which ensures a better collapsing to create the seal during the mixing of the bone cement as is further detailed subsequently. The elastomeric material for the valve can also be provided with a shape memory to facilitate the collapse of the valve as further described and illustrated.

Figure 1B:
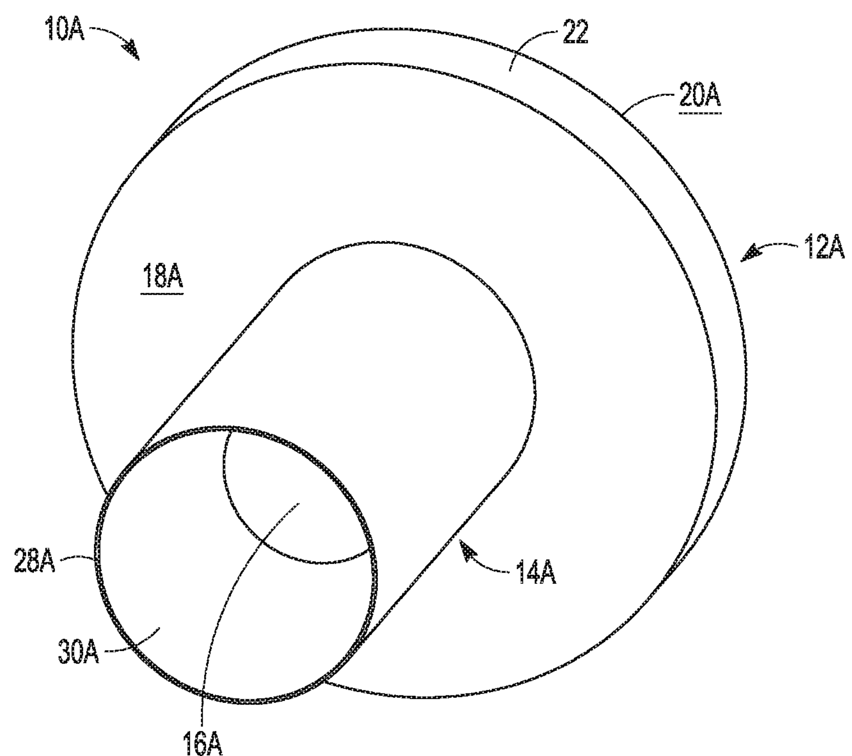
Figure 1C:
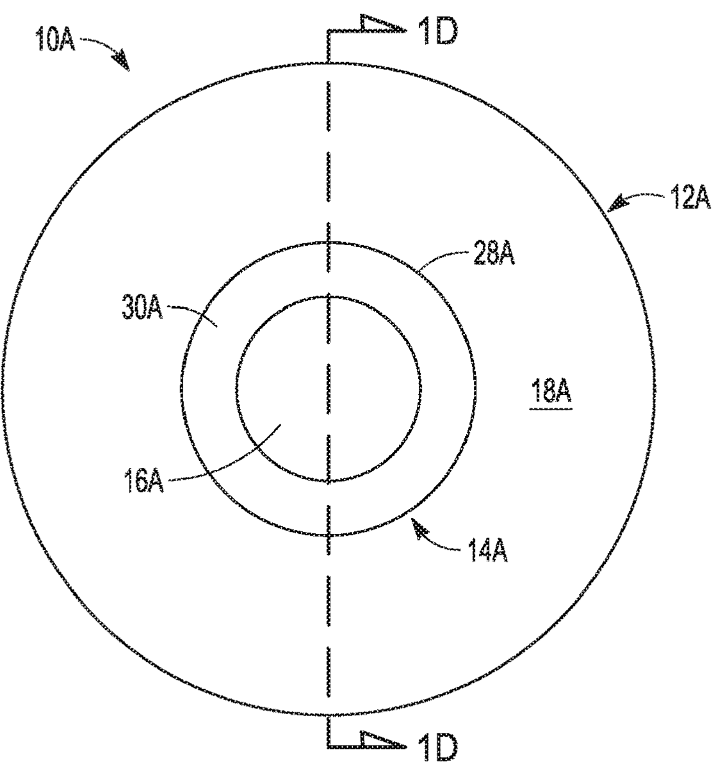
Figure 1D:
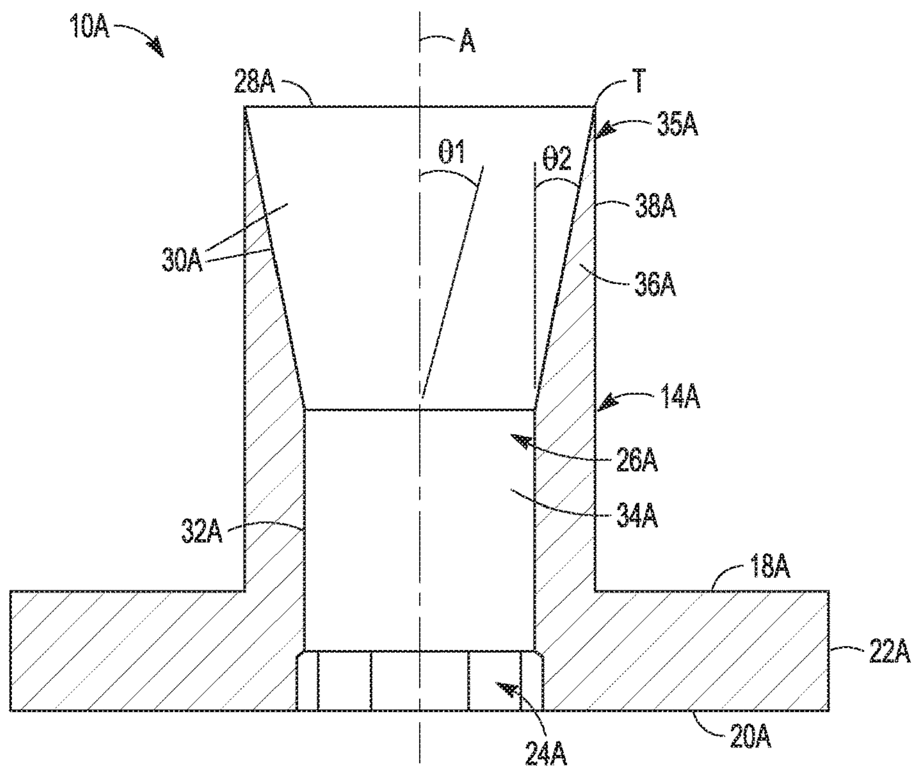

Turning now to the figures, FIGS. 1A-1D show a valve 10A from various perspectives. In particular, FIGS. 1A and 1B are elevated perspective views of the valve 10A. FIG. 1C is a plan view of the valve 10A from a first side. FIG. 1D is a cross-sectional view of the valve 11.0A along the section 1D-1D of FIG. 1C.

As shown in FIGS. 1A-1D, the valve 10A can include a base 12A and a projection 14A that are interconnected with one another and can be integrally formed as a single piece. Together, the base 12A and projection 14A can form a passage 16A that can extend through the valve 10A. The passage 16A can be configured to allow a component of the bone cement (e.g., a liquid or monomer) through the valve 10A as discussed subsequently.

The base 12A can comprise a generally cylindrical shaped component having a first generally flat circular surface 18A, a second generally flat circular surface 20A (FIGS. 1A, 1B and 1D) and a side surface 22A. The second surface 20A can oppose the first surface 18A and the side surface 22A can extend between the first surface 18A and the second surface 20A.

As shown in FIG. 1D the base 12A can define a first portion 24A of the passage 16A and the projection 14A can define a second portion 26A of the passage 16A. The first portion 24A can communicate with the second portion 26A. Thus, the passage 16A can he defined by both the base 12A and the projection 14A. The projection 14A can extend from the base 12A, and in particular, from the first surface 18A. The projection 14A can extend from the base 12A to a base opposing end 28A (i.e. a tip of the valve 10A).

The valve 10A, including the projection 14A, can comprise an elastomeric material such as one of silicone, polyacrylate, EPDM, FKM, and/or nitrile NBR, for example. In the example of FIGS. 1A-1D the projection 14A can be formed of elastomeric material having a shape memory configured to collapse the projection 14A to seal the passage 16A at the base opposing end 28A of the projection 14A.

As shown in FIGS. 1A-1D, the projection 14A can have a frustoconically shaped surface 30A. In the example of FIGS. 1A-1D the frustoconically shaped surface 30A can be a portion of an interior surface 32A that forms at least a part of the second portion 26A of the passage 16A. In the example of FIGS. 1A-1D, the frustoconically shaped surface 30A can extend to the base opposing end 28A. A length of the frustoconically shaped surface 30A along a longitudinal axis A (FIG. 1D) can be between 4 mm and 8 mm, for example. According to one example, the length of the frustoconically shaped surface 30A along a longitudinal axis A can be between 20% and 100%, inclusive, of a total length of the projection 14A The projection 14A can extend along the longitudinal axis A as shown in FIG. 1D. Such axis A can comprise an axis of symmetry of the projection 14A. An axis of symmetry of the passage 16A (not shown) can be co-aligned with that of the axis A. In FIG. 1D, the frustoconically shaped surface 30A can have an angle θ1 of between 5 degrees and 35 degrees, inclusive relative to the axis A. In further examples, the angle θ1 can be between 10 degrees and 30 degrees, inclusive. Described another way, the frustoconically shaped surface 30A can have an angle θ2 relative to a cylindrically shaped surface 34A of the projection 14A to which it connects. In the example of FIG. 1D, the cylindrically shaped surface 34A comprises part of the interior surface 32A positioned proximal of the frustoconically shaped surface 30A.

In the example of FIG. ID, the projection 14A can have a circular shape in cross-section at the base opposing end 28A, thus an end portion 35A that forms the base opposing end 28A can have a cylindrical surface along at least one of the interior surface 32A or an exterior surface 38A of the projection 14A. In some examples such as that of FIG. 3, the end portion 35A can be cylindrically shaped along both the interior surface 32A and the exterior surface 38A of the projection 14A. However, in FIG. 1D a wall 36A that forms the end portion 35A of the projection 14A including the base opposing end 28A can be cylindrically shaped along one of the exterior surface 38A or the interior surface 32A. The wall 36A can extend between the interior surface 32A and the exterior surface 38A of the projection 14A. In the example of FIG. 1D, the wall 36A can have a thickness T at the base opposing end 28A of between 0.075 mm and 0.30 mm, inclusive. However, the inventors determined that the thickness at a lower end of the range provided above can offer better results in providing a seal as discussed subsequently.

Figure 2:
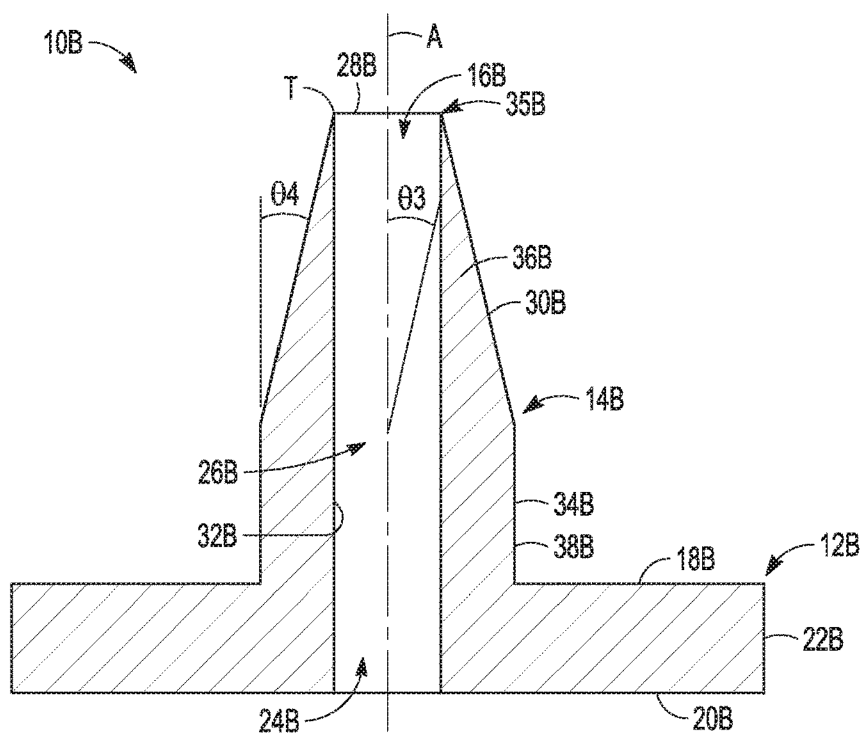
FIG. 2 shows a cross-section of a second valve according to another example of the present disclosure.

FIG. 2 shows a cross-section of a valve 10B according to another example of the present application. The valve 10B can have a construction similar to that of the valve 10A of FIGS. 1A-1D save the frustoconically shaped surface 30B can be part of an exterior surface 38B of a projection 14B. Thus, the valve 10B can include a base 12B, the projection 14B, a passageway 16B, a first surface 18B, a second surface 20B, a side surface 22B, a first portion 24B, a second portion 26B, a base opposing end 28B, the frustoconically shaped surface 30B, an interior surface 32B, a cylindrically shaped surface 34B, a wall 36B and the exterior surface 38B. These features can be constructed similar to the corresponding numbered features of the example of FIGS. 1A-1D with only some slight modification of some of the features as noted below and above.

The example of FIG. 2 differs slightly from the example of FIGS. 1A-1D in the frustoconically shaped surface 30B can be a portion of the exterior surface 38B of the projection 14A. In the example of FIG. 2, the frustoconically shaped surface 30B can extend to the base opposing end 28B. The projection 14B can extend along the longitudinal axis A as shown in FIG. 2. Such axis A can comprise an axis of symmetry of the projection 14B. An axis of symmetry of the passage 16B (not shown) can be co-aligned with that of the axis A. In FIG. 2, the frustoconically shaped surface 30B can have an angle θ3 of between 5 degrees and 35 degrees, inclusive relative to the axis A. In further examples, the angle θ3 can be between 10 degrees and 30 degrees, inclusive. Described another way, the frustoconically shaped surface 30B can have an angle θ4 relative to the cylindrically shaped surface 34B of the projection 14B to which it connects. As discussed above, in the example of FIG. 2 the cylindrically shaped surface 34B comprises part of the exterior surface 38B positioned proximal of the frustoconically shaped surface 30B.

Similar to the projection 14A, the projection 14B can have a circular shape in cross-section at the base opposing end 28B, thus the end portion 35B that forms the base opposing end 28B can have a cylindrical surface along at least one of the interior surface 32B or the exterior surface 38B. In FIG. 2, the wall 36B that forms the end portion 35B of the projection 14B including the base opposing end 28B can be cylindrically shaped along one of the exterior surface 38B or the interior surface 32B. The wall 36A can extend between the interior surface 32A and the exterior surface 38A of the projection 14A. In the example of FIG. 1D, the wall 36A can have a thickness T at the base opposing end 28A of between 0.075 mm and 0.30 mm, inclusive.

Figure 3:
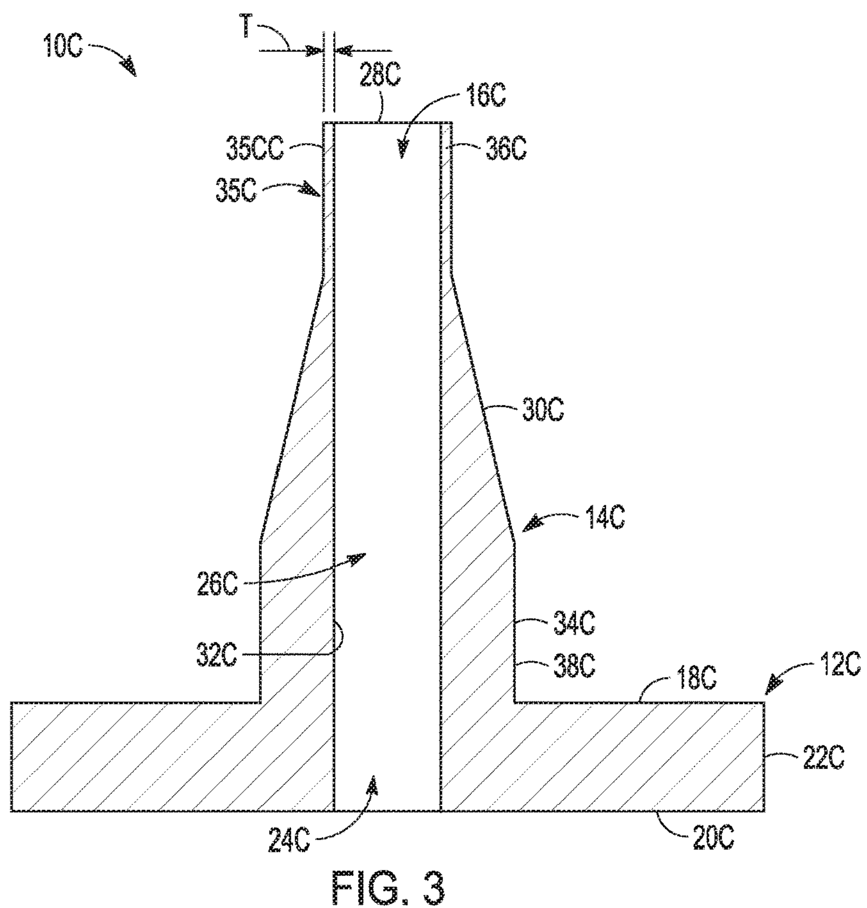
FIG. 3 shows a cross-section of a third valve according to yet another example of the present disclosure.

Turning to FIG. 3, FIG. 3 shows a cross-section of a valve 10C according to another example of the present application, The valve 10C can have a construction similar to that of the valve 10B of FIGS. 1B save the end portion 35C can comprise a cylindrically shaped portion 35CC having both an exterior surface 38C and an interior surface 32C of a projection 14B being cylindrical. Thus, the valve 10C can include a base 12C, the projection 14C, a passageway 16C, a first surface 18C, a second surface 20C, a side surface 22C, a first portion 24C, a second portion 26C, a base opposing end 28C, the frustoconically shaped surface 30C, the interior surface 32C, a cylindrically shaped surface 34C, the cylindrical portion 35C, a wall 36C and the exterior surface 38C. These features can be constructed similar to the corresponding numbered features of the example of FIG. 2 with only some slight modification of some of the features as noted below and above.

In the example of FIG. 3, the projection 14C can have a circular shape in cross-section at the base opposing end 28C, thus the end portion 35C that forms the base opposing end 28C can comprise the cylindrical portion 35CC, which can have a cylindrical surface along both of the interior surface 32C and the exterior surface 38C of the projection 14C, Thus, in FIG. 3 the wall 36C that forms the end portion 35C including the base opposing end 28C can be cylindrically shaped along both of the exterior surface 38C and the interior surface 32C. The wall 36C can extend between the interior surface 32C and the exterior surface 38C of the projection 14C. In the example of FIG. 1D, the wall 36C can have a thickness T at the base opposing end 28C of between 0.075 mm and 0.30 mm, inclusive. The length of the cylindrical portion 35CC can be between 10% and 30%, inclusive, of the total length of the projection 14C.

Figure 4:
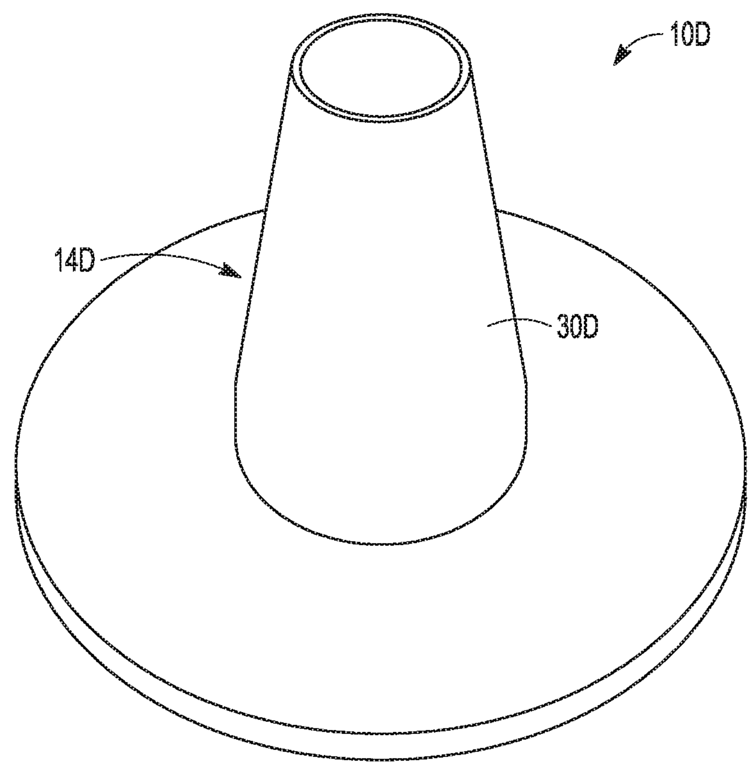
FIG. 4 shows a fourth valve according to another example of the present disclosure.

FIG. 4 shows yet another valve 10D where the frustoconically shaped surface 30D extends substantially an entire longitudinal length of the projection 14D.

Figure 5:
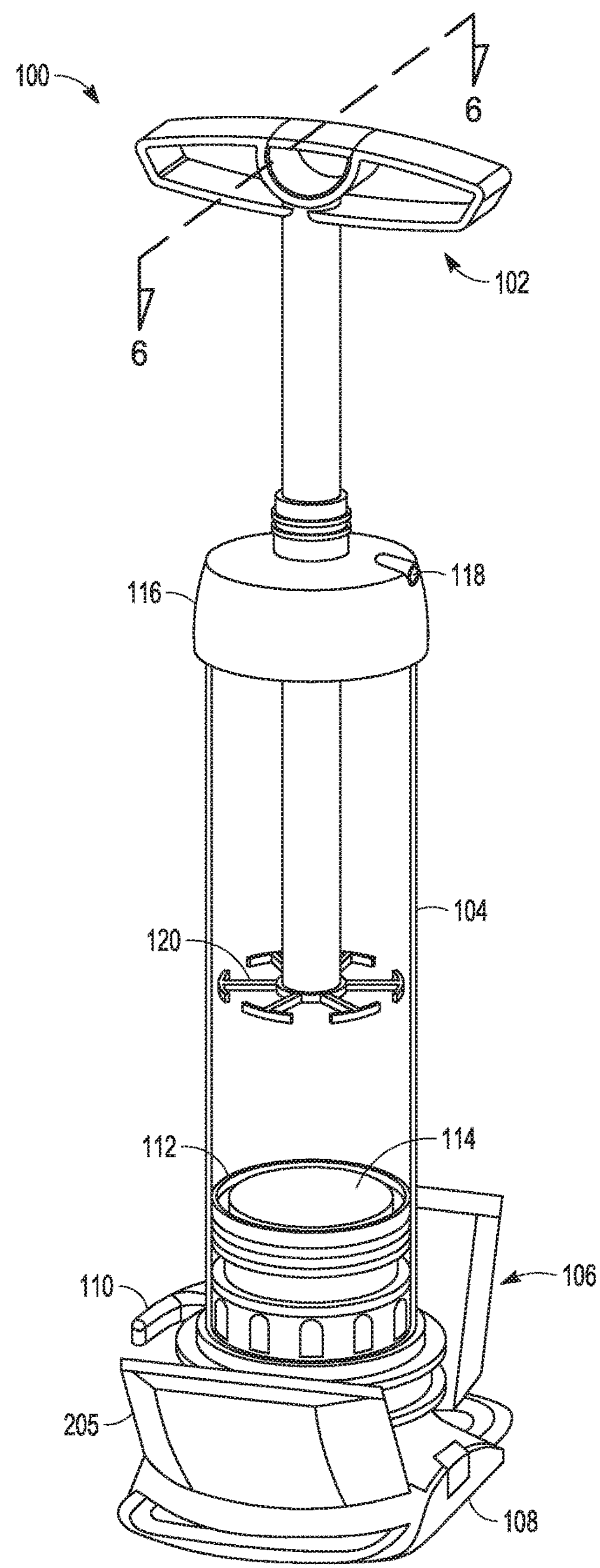
FIG. 5 shows an example system including an apparatus for mixing bone cement in accordance with at least one example of the present disclosure.

FIG. 5 shows an apparatus 100 for mixing bone cement in accordance with at least one example of the present disclosure. The apparatus 100 can include one or more of the valves 10A-10D as previously described. As shown in FIG. 5, the apparatus 100 can include a handle 102, a mixing chamber 104, a connecting cylinder 106, a base 108, and a safety strip 110. A piston 112 can be located within the mixing chamber 104 and a filter 114 can be located on top of the piston 112. The handle 102 can pass through a cap 116 that can seal a portion of the mixing chamber 104. As discussed herein, the cap 116 can include a vacuum port 118 that can be used to connect the apparatus 100 to a vacuum pump (not shown) to create a vacuum within the mixing chamber 104.

The safety strip 110 can be a flexible member that slips around a portion of the base 108. For example, the safety strip 110 can partially surround the base 108 and rest between the connecting cylinder 106 and a portion of the base 108, such as flared portions 812 to hinder movement of the base 108. The safety strip 110 can also act as a tamper detection device. For example, the safety strip 110 can be formed such that removal of the safety strip 110 would result in inelastic deformation of the safety strip 110. As such, removal and replacement of the safety strip 110 would be evident to the surgeon or others upon visual inspection.

The handle 102 can be connected to a mixer 120. After bone cement components have been introduced into the mixing chamber 104, the handle 102 can be articulated such that the mixer 120 moves along a longitudinal axis of the mixing chamber 104. The movement of the mixer 120 can allow the bone cement components to be mixed such that a homogenous mixture is created.

The walls defining the mixing chamber 104 can be opaque or transparent. Transparent walls, such as shown in FIG. 5 can allow the surgeon to view the bone cement during a mixing process. By allowing the surgeon to view the bone cement, the surgeon can determine when the bone cement components have been thoroughly mixed. In addition, the surgeon can determine an amount of bone cement remaining in the mixing chamber 104. For example, once the mixing chamber 104 has been transferred to an applicator (not shown), the surgeon can utilize a transparent mixing chamber 104 to determine if he or she has enough bone cement for a procedure to be undertaken. For instance, after installing a tibial component of a knee implant, the surgeon can view a remaining amount of bone cement in the mixing chamber 104 to determine if he or she has enough bone cement remaining to install a femoral component of the knee implant or if more bone cement needs to be mixed.

Figure 6:
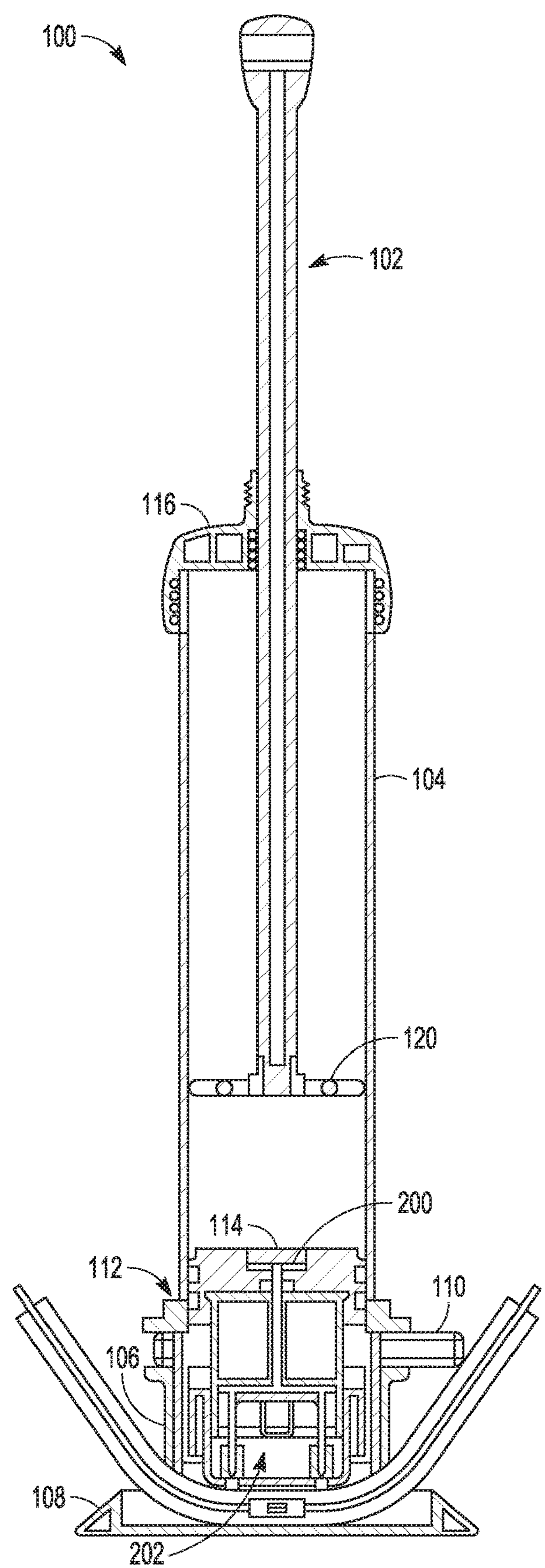
FIG. 6 shows an example of a cross-section of the apparatus for mixing bone cement in accordance with at least one example of the present disclosure.
Figure 7:
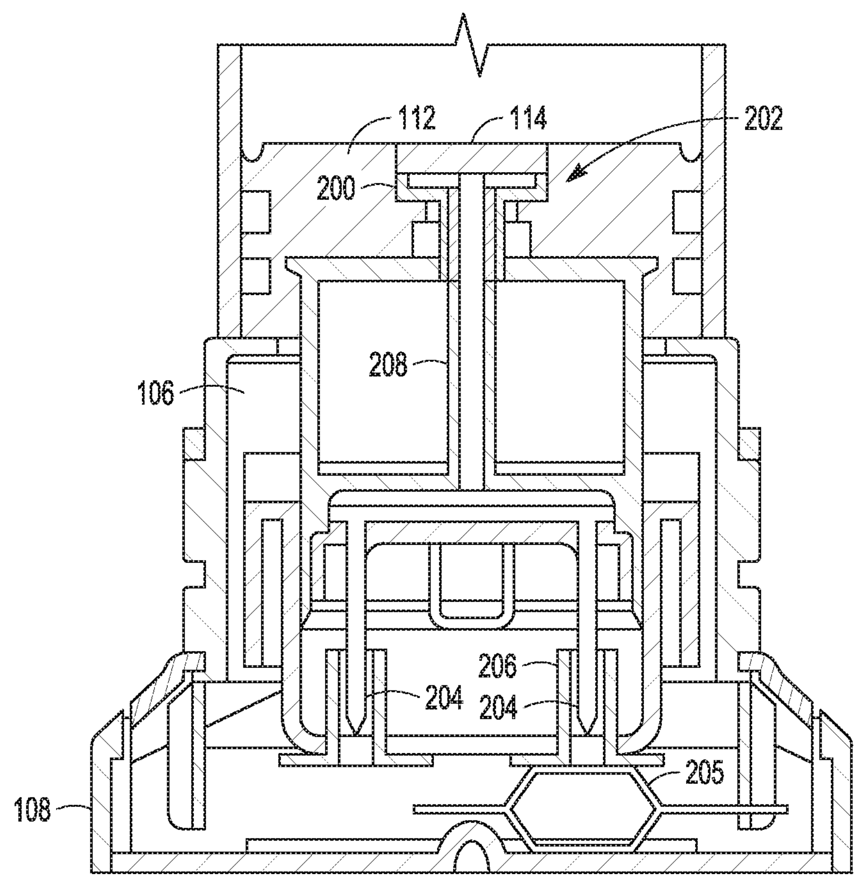
FIG. 7 shows a detail of a valve assembly in accordance with at least one example of the present disclosure.

FIG. 6 shows a cross section of the apparatus 100 in accordance with at least one example of the present disclosure. As shown in FIG. 6, the apparatus 100 can include a valve assembly 202 with a valve 200 such as the valves 10A-10D previously described. In addition, a pouch 205 can be partially located in the base 108 (pouch 205 is also shown in FIG. 5). FIGS. 7, 9A, 9B, and 13A-13C show the valve assembly 202 in accordance with at least one example of the present disclosure in greater detail. As shown in FIG. 7, the valve assembly 202 can include the valve 200 as previously described in reference to FIGS. 1A-4, the piston 112, the filter 114, cannulas 204, and seals 206. The connecting cylinder 106 can define a conduit 208 that can allow fluid communication between an interior portion of the connecting cylinder 106 and the mixing chamber 104.

Figure 9A:
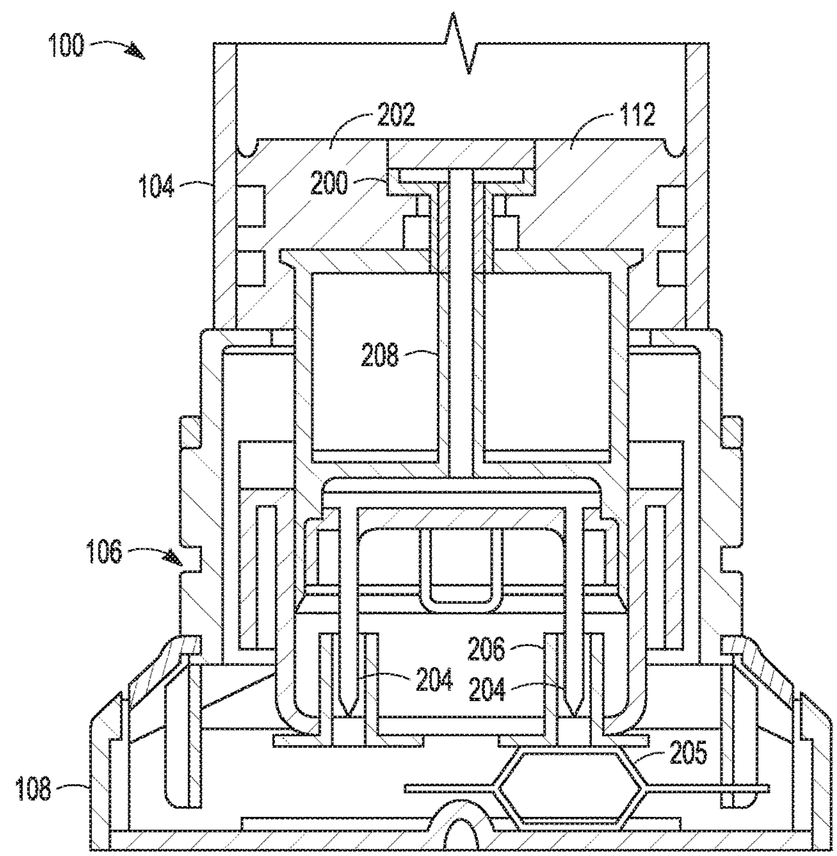
FIGS. 9A and 9B show the valve assembly including during the initiation of the mixing process where a component of the bone cement is passed through a conduit and valve into the mixing chamber in accordance with at least one example of the present disclosure.

As shown in FIGS. 7 and 9A, the apparatus 100 can be shipped with the base 108 partially inserted within the connecting cylinder 106. The safety strip 110 can hinder movement of the base 108 relative to the connecting cylinder 106. The safety strip 110 can be removed and movement of the base 108 can allow the cannulas 204 to puncture the pouch 205 and allow the contents of the pouch 205 to flow into the mixing chamber as described below.

Figure 8:
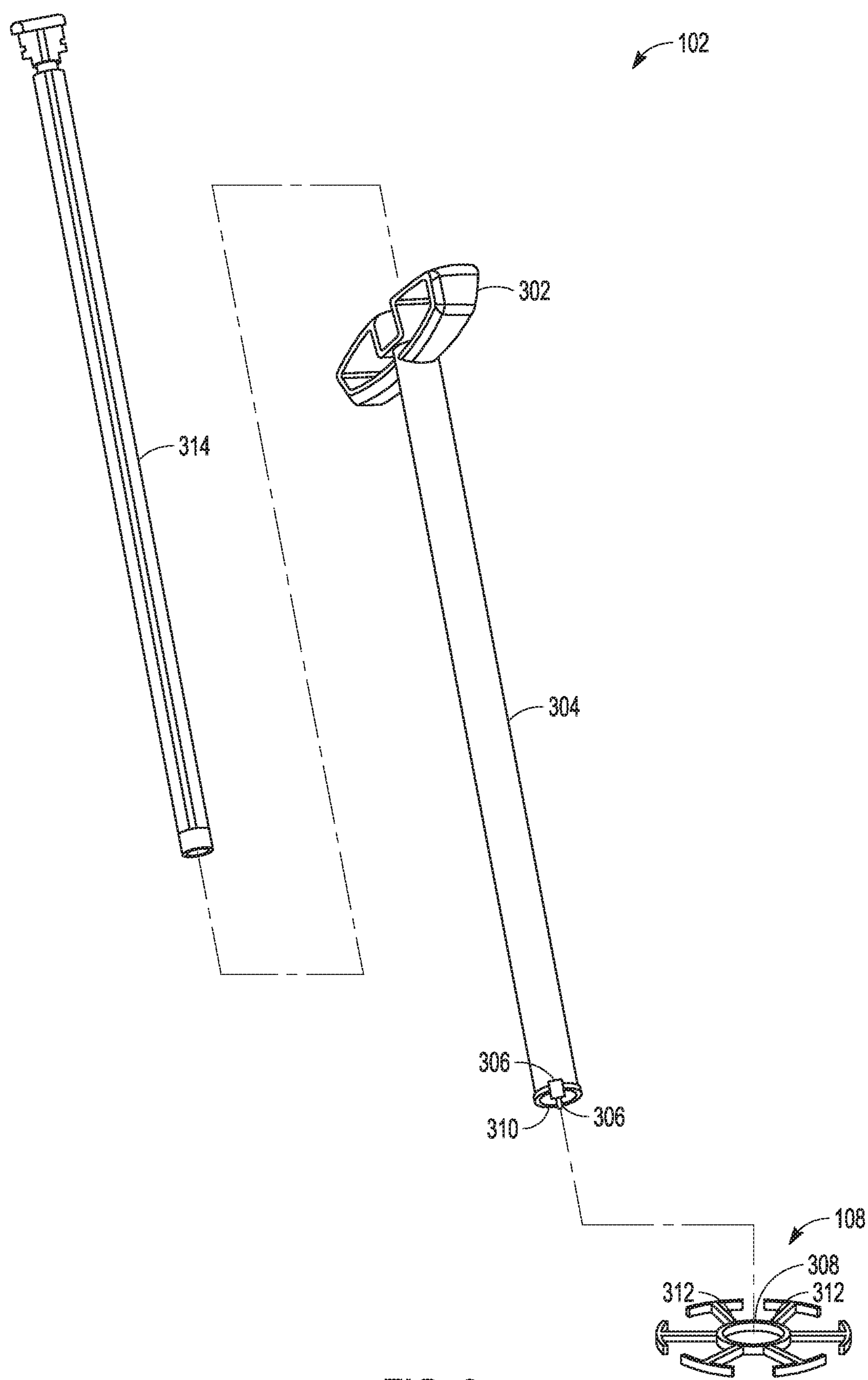
FIG. 8 shows an example exploded assembly of a handle and a mixer in accordance with at least one example of the present disclosure.

FIG. 8 shows an example exploded assembly of the handle 102 and the mixer 120. As shown in FIG. 8, the handle 102 can include a grip 302 and a cannulated rod 304. The cannulated rod 304 can include one or more flexible fingers 306 that can engage an inner surface 308 of the mixer 120. In addition, the cannulated rod 304 can define one or more notches 310 that can engage one or more protrusions 312 extending from the inner surface 308.

The mixer 120 can be attached to the cannulated rod 304 by pressing the mixer 120 onto the flexible finger 306. Once the mixer 120 is attached to the cannulated rod 304, an inner rod 314 can be inserted into the cannulated rod 304. The inner rod 314 can include a solid portion316 that can rest against the flexible fingers 306. Once inserted, the solid portion 316 can prevent the flexible fingers from flexing inward, thus securing the mixer 120 to the cannulated rod 304.

The grip 302, the cannulated rod 304, the inner rod 314, and the mixer 120 can be manufactured from polymers, metals, ceramics, or combinations thereof. For example, the grip 302, the cannulated rod 304, and the mixer 120 can be manufactured from a surgical grad stainless steel or titanium and the inner rod 314 can be manufactured from a polymer. The grip 302, the cannulated rod 304, the inner rod 314, and the mixer 120 can be manufactured from a variety of manufacturing techniques that include, but are not limited to, injection molding, over molding, machining, casting etc. For example, the cannulated rod 304 and the mixer 120 can each be machined using a computer numerical controlled (CNC) mill and the grip 302 can be over-molded to a portion of the cannulated rod 304.

The mixing chamber 104 can include threads located at a first end of the mixing chamber 104. The threads can cooperate with threads located on the cap 116 such that the cap 116 can be screwed to the mixing chamber 104. The mixing chamber 104 can also include ribs. As described herein, the ribs can be used to secure and rotate the piston 112 via the connecting cylinder 106 and for mounting the mixing chamber 104 to an applicator (not shown).

As discussed herein, the mixing chamber 104 can be opaque or transparent. The mixing 104 chamber can be manufactured from polymers, metals, ceramics, or a combination thereof. For example, the mixing chamber 104 can be manufactured from a biocompatible polymer or metal. For instance, the mixing chamber 104 can be manufactured from titanium such that the mixing chamber 104 can be sterilized for use with multiple patients. In addition, the mixing chamber 104 can be manufactured from a variety of manufacturing techniques including, but not limited to, machining, injection molding, etc. For example, the mixing chamber 104 can be injection molded from a transparent polymer.

As disclosed herein the cap 116 can define a through hole that can allow the mixed bone cement to exit the mixing chamber 104 and the cannulated rod 304 and the inner rod 314 to pass through the cap. For example, as disclosed herein the cannulated rod 304 an be separated from the mixer 120 and the cannulated rod 304 can then be pulled through the through hole and. removed from the mixing chamber as described above. The cap 116 can also include threads that can allow a nozzle (not shown) to be connected to the cap 116. The nozzle can be used by the surgeon to direct the bone cement.

The cap 116 can be manufactured from polymers, metals, ceramics, or a combination thereof. For example, the cap 116 can be manufactured from a biocotnpatible polymer or metal. For instance, the cap 116 can be manufactured from titanium such that the cap 116 can be sterilized for use with multiple patients. In addition, the cap 116 can be manufactured from a variety of manufacturing techniques including, but not limited to, machining, injection molding, etc. For example, the cap 116 can be injection molded from a polymer.

The cannulas 204 can each include a collar and a tip. The cannulas 204 can be press fit into the connecting cylinder 106. The tip can be sharp such that the tip can puncture the pouch 205 when the base 108 is inserted into the connecting cylinder 106.

The cannulas 204 can be manufactured from metals, polymers, ceramics, or combinations thereof. The cannulas 204 can be manufactured from a variety of manufacturing techniques including, but not limited to, stamping, machining, and injection molding.

The connecting cylinder 106 can include one or more protrusions. The protrusions can engage the piston 112 located in the mixing chamber 104. In addition, as discussed herein, the protrusions can allow for the piston 112 to be attached to the connecting cylinder 106.

The connecting cylinder 106 can be manufactured from metals, polymers, ceramics, or combinations thereof The connecting cylinder 106 can be manufactured from a variety of manufacturing techniques including, but not limited to, stamping, machining, and injection molding, etc.

The piston 112 can include notches that can engage the protrusions of the connecting cylinder 106. Connecting the piston 112 to the connecting cylinder 106 can prevent the piston 112 from moving while the apparatus 100 is in transport or while the vacuum is created in the mixing chamber 104. The piston 112 can also include a peg that peg can engage the ribs as described below. By engaging the ribs, the peg can allow the connecting cylinder 106 to be rotated without rotating the piston 112.

Rotation of the connecting cylinder 106 without rotation of the piston 112 can allow the protrusions to disengage from the notches. With the protrusions disengaged from the notches, the connecting cylinder 106 can be removed from the mixing chamber 104. As disclosed herein, removal of the connecting cylinder 106 can allow the piston 112 to move due to the negative pressure created by the vacuum within the mixing chamber 104 and the valve 200 to close thereby sealing the mixing chamber 104. Closing of the valve 200 will be described in further detail subsequently. The piston 112 can also include a recess, that can allow the valve 200 and the filter 114 to rest within the piston 112. The piston 112 can also include one or more grooves. The grooves can allow O-rings or other sealing devices to be installed to seal the interface between the piston 112 and an inner surface of the mixing chamber 104 while still allowing the piston 112 to move. Movement of the piston 112 towards the cap 116 can force the bone cement from the mixing chamber 104.

The piston 112 can be manufactured from metals, polymers, ceramics, or combinations thereof. The piston 112 can be manufactured from a variety of manufacturing techniques including, but not limited to, machining and injection molding.

Figure 9B:
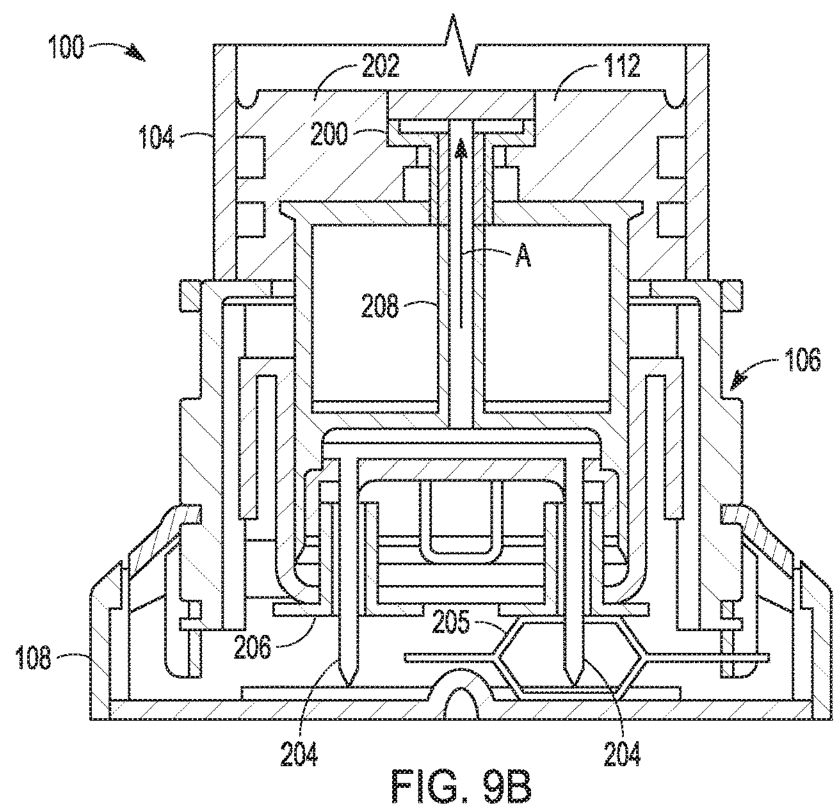

FIGS. 9A and 9B show the apparatus 100 as previously shown and described in FIG. 7 before puncturing of the pouch 205 (state of FIG. 9A) and after puncture of the pouch (state of FIG. 913) by one or more of the cannulas 204. The FIG. 913 also show flow of a component (e.g., liquid or monomer) through the valve 200 to the mixing chamber 104 as indicated by arrow A. FIGS. 9A and 9B will be discussed subsequently.

Figure 10:
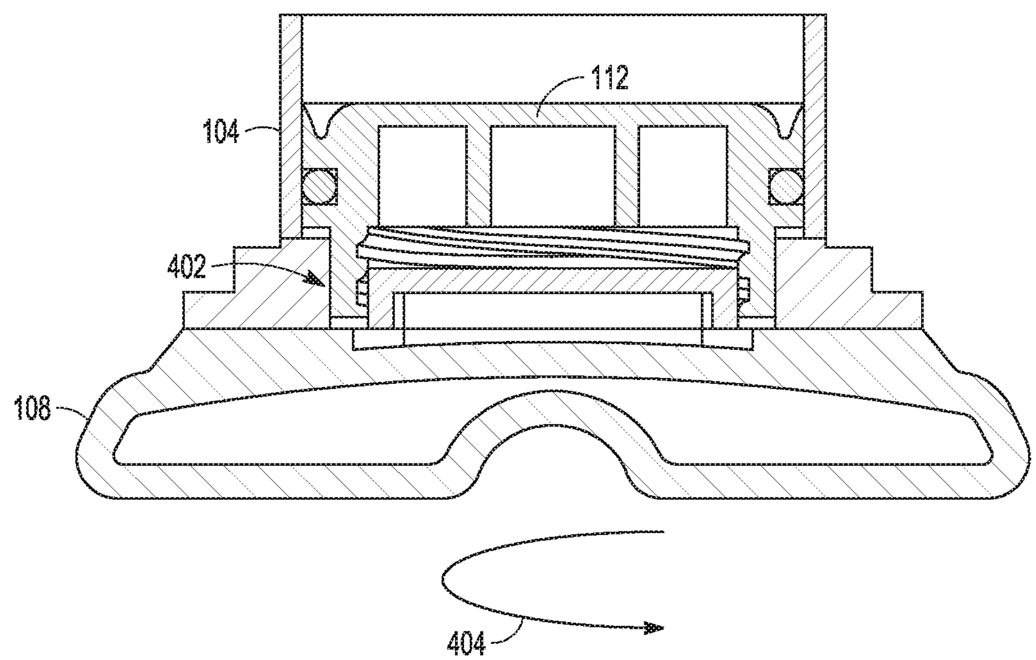
FIGS. 10 and 11 show an example of a base in accordance with at least one example of the present disclosure.
Figure 11:
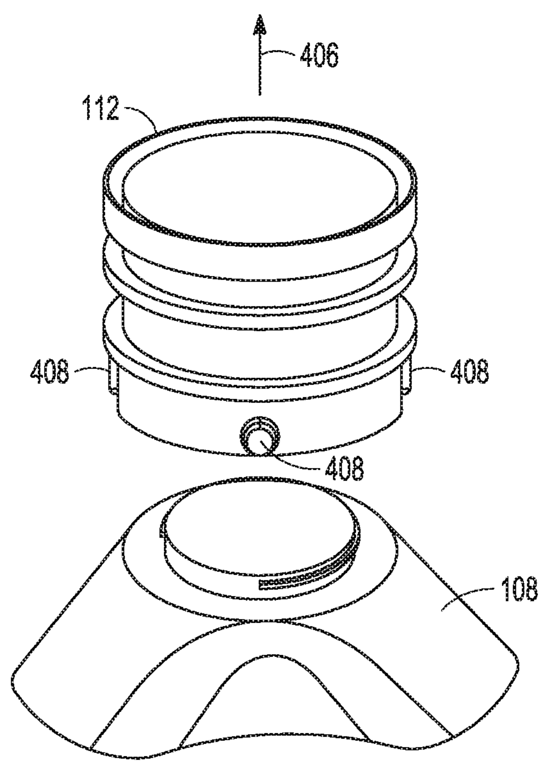

As shown in FIG. 10, in some examples the base 108 can be connected to the piston 112 via a threaded section 402. Once the bone cement has been mixed, the base 108 can be unscrewed from the piston 112 as indicated by arrow 404. The vacuum created via the vacuum port can cause the piston 112 to travel towards the cap as indicated by arrow 406 in FIG. 11. As shown in FIG. 11, the piston 112 can include one or more protrusions 408. The protrusions 408 can engage one or more grooves in the mixing chamber 104 as disclosed herein to prevent the piston 112 from rotating as the base 108 rotates.

Figure 12:
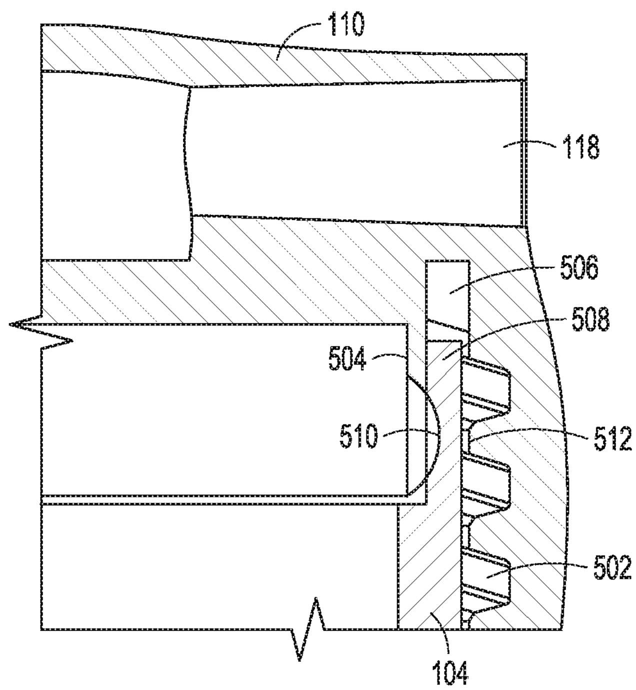
FIG. 12 shows an example cross-section of a cap in accordance with at least one example of the present disclosure.

FIG. 12 shows a cross-section of the cap 116 with the port 118 according to one example. The cap 116 can include a threaded section 502 and an extended portion 504. The threaded section 502 and the extended portion 504 can define a recess 506. As the cap 116 can be threaded onto the mixing chamber 104, a rim 508 of the mixing chamber 104 can slid into the recess 506. The extended portion 504 can define a protrusion 510 that can rest in an indentation 512 defined by the rim 508. The protrusion 510 and the indentation 512 can form an airtight seal, without the use of O-rings or other sealants, which can allow the vacuum to be form as well as prevent the bone cement from leaking from the mixing chamber 104.

As disclosed herein, the cap 116 can be manufactured from a polymer, metal, or ceramic. In addition, the cap 116 can be manufactured via manufacturing methods includes, but not limited to, injection molding, over-molding, machining, and the like. For example, the cap 116 can be made of a polymer via injection molding.

Figure 13A:
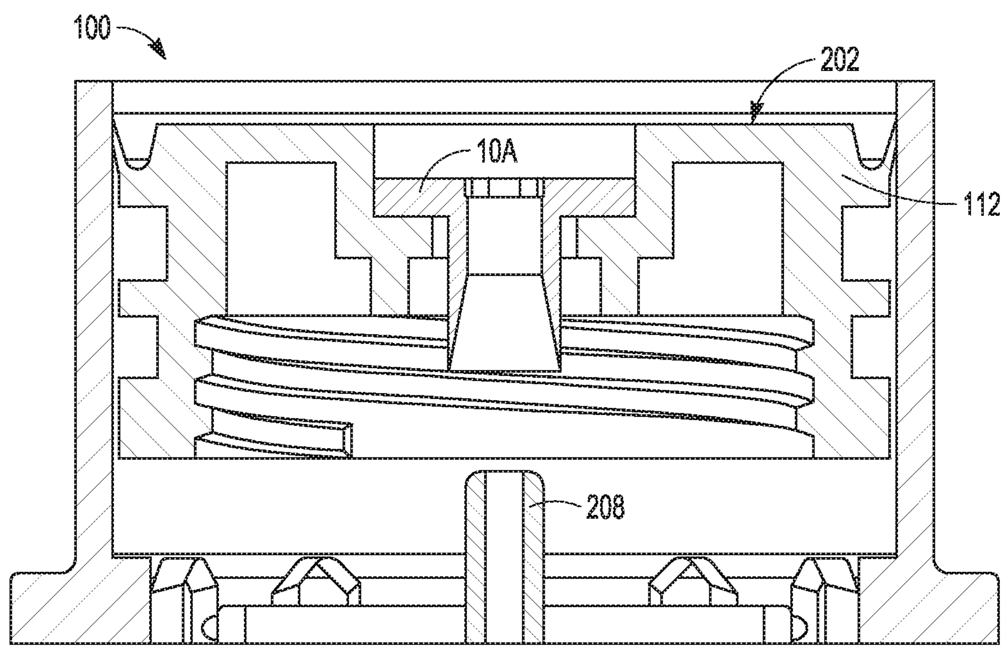
FIGS. 13A-13C show an enlargement of the valve assembly including prior to an initial assembly (FIG. 13A), upon shipping and during initiation of the mixing process (FIG. 13B), and during the mixing process (FIG. 13C) where a projection of the valve has collapsed to seal a passage through the valve and thereby seal the mixing chamber according to an example of the present disclosure.
Figure 13B:
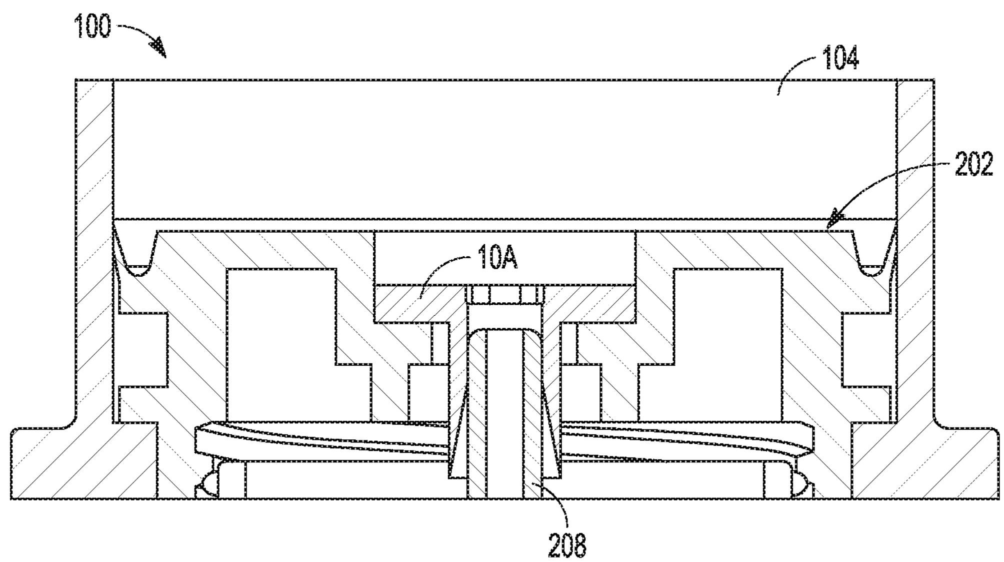

FIG. 13A shows the apparatus 100 with the valve assembly 202 including the valve 10A as previously described during a pre-assembly (i.e., pre-shipping to the customer) by a manufacturer. In such position, the piston 112 and the valve 10A can be spaced from the conduit 208. The piston 112 can then be brought down into position such that the valve 10A receives a portion of the conduit 208 therein as shown in FIG. 13B. The valve 10A is configured to receive the conduit 208 without damage thereto. Once in the position shown in FIG. 13B, the valve 10A can be configured to form a seal with the conduit 208 so that no air or other material can enter the mixing chamber 104 that houses a first component of the bone cement. In the position of 13B, the apparatus 100 can be shipped. As previously described, the safety strip 110 (FIGS. 5-6) can hinder movement of the base 108 (FIGS. 5-6) relative to the connecting cylinder 106 (FIG. 5-6) such that the pouch 205 is not punctured by accident. Thus, FIG. 13B is an enlarged view of the apparatus 100 in the configuration of FIG. 9A.

FIGS. 9A, 9B and 13B and 13C will now be referenced in conjunction with an example of how the apparatus 100 facilitates mixing bone cement in accordance with at least one example of the present disclosure.

As previously discussed, the apparatus 100 can be shipped to the customer in the state of FIGS. 9A and 13B where no mixing of the components of the bone cement has occurred. Should such mixing be desired, a vacuum can be created within the mixing chamber 104 and the valve assembly 202. As indicated above, the vacuum port 118 (FIGS. 5 and 12) can be connected to a vacuum pump (not shown) in order to create a vacuum within the mixing chamber 104. The vacuum pump can be a hand operated pump or an electric pump.

As shown in FIG. 9B, the pouch 205 can be punctured facilitated by removal of the safety strip 110 (FIG. 5). In particular, the pouch 205 can be punctured by one or more of the cannulas 204. As shown in FIG. 9B, the base 108 can be moved co-axially relative to the connecting cylinder 106, which can cause one or more of the cannulas 204 to puncture the pouch 205.

Once the pouch 205 is punctured, a second component of the bone cement formerly only housed within the pouch 205 can be caused to pass from the pouch 205 into the mixing chamber 104. For example, upon puncturing of the pouch 205, the vacuum created in the mixing chamber 104 and the valve assembly 202 can draw the second component located in the pouch 204 into the mixing chamber 104 via one or more of the cannulas 204 and conduit 208. For instance, the second component located in the pouch 205 can be a liquid monomer used as a curing agent or an epoxy for binding the first component of the bone cement already located within the mixing chamber 104. The pressure difference created by the vacuum can cause the second component to flow from the pouch 205 through the cannula 204, and the conduit 208 into the mixing chamber 104. To facilitate fluid flow, the pouch 205 can be a flexible or otherwise deformable structure. Once the pouch 205 is punctured, the volume of the pouch 205 can decrease as the second component of the bone cement is drawn into the mixing chamber 104.

As shown in FIGS. 9B and 13B, the pouch 205 and the one or more cannulas 204 can be configured to form seal 206 such that once the pouch 205 is punctured, the second component of the bone cement is forced through the seal 206 and does not leak into the interior portion of the base 108. In addition, this seal along with the seal formed by the valve 10A with the conduit 208 can prevent air from entering the mixing chamber 104. Stated another way, these seals help maintain the vacuum created in the mixing chamber 104 and the valve assembly 202 when the pouch 205 is punctured.

The first component of the bone cement and the second component of the bone cement can be mixed within the mixing chamber 104. As indicated above, the handle 102 can be articulated to cause movement of the mixer 120 to mix the first component and the second component. In addition, the mixing chamber 104 could be agitated to mix the first component and the second component.

Figure 13C:
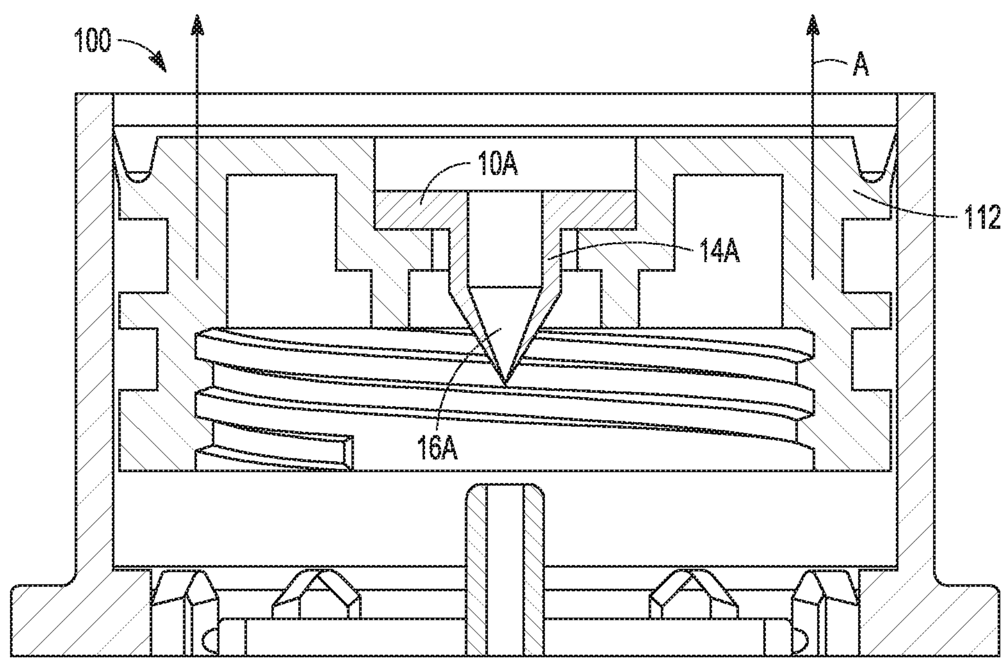

The mixing chamber 104 can be sealed during the mixing process. As shown in FIG. 13C, the piston 112 can be moved away from the base 108 (FIGS. 9A and 9B) or, the connecting cylinder 106 (FIGS. 9A and 9B) including the base 108 as indicated by arrow A. The movement of the piston 112 can cause the valve 10A to close via a collapse of the projection 14A at the tip. This collapse of the projection 14A can seal the passage 16A as previously discussed. The filter 114 along with the valve 10A can help prevent the first component of the bone cement from exiting the mixing chamber 104 through the piston 112. The movement of the piston 112 can be caused by the vacuum created within the mixing chamber 104 or by removing the base 108 from the connecting cylinder 106. For example, as discussed above, the piston 112 can be secured to the base 108 and removing the base 108 from the connecting cylinder 106 can allow the piston to move due to the vacuum created within the mixing chamber 104 or by an external force applied by the surgeon. The movement of the piston 112 can cause the valve 10A to close via the collapse of the projection 14A at the tip, thereby sealing the piston 112 and the mixing chamber 104.

It will be readily understood to those skilled in the art that various other changes in the details, material, and arrangements of the parts and method stages which have been described and illustrated in order to explain the nature of the inventive subject matter may be made without departing from the principles and scope of the inventive subject matter as expressed in the subjoined claims.

To better illustrate the apparatuses including valves and other systems and assemblies disclosed herein, a non-limiting list of examples is provided here:

In Example 1, a valve for an apparatus configured to mix bone cement, the valve can optionally include: a base defining a first portion of a passage, the passage is configured to allow a component of the bone cement through the valve; and a projection extending from the base to a base opposing end and forming a second portion of the passage that communicates with the first portion, the projection having a frustoconically shaped surface that comprises one of an outer surface or an inner surface that forms a part of the second portion of the passage.

In Example 2, the valve of Example 1, wherein the frustoconically shaped surface can optionally have an angle of between 5 degrees and 35 degrees, inclusive, relative to a longitudinal axis of the projection.

In Example 3, the valve of any one or any combination of Examples 1-2, wherein the frustoconically shaped surface can optionally have an angle of between 5 degrees and 35 degrees, inclusive, relative to a cylindrically shaped surface of the projection:

In Example 4, the valve of any one or any combination of Examples 1-3, wherein the projection can optionally have a first cylindrical portion forming the base opposing end of the projection.

In Example 5, the valve of Example 4, wherein the first cylindrical portion can optionally have a longitudinal length of between 10% and 30%, inclusive, of a total longitudinal length of the projection.

In Example 6, the valve of any one or any combination of Examples 1-3, wherein the frustoconically shaped surface can optionally extend to the base opposing end of the projection.

In Example 7, the valve of any one or any combination of Examples 1-5, wherein the projection can be formed of ela.stomeric material having and can have a shape memory configured to collapse the projection to seal the passage at the base opposing end of the projection.

In Example 8, the valve of Example 6, whereine the elastomeric material can comprise silicone.

In Example 9, the valve of any one or any combination of Examples 1-6, wherein a thickness of a wall of the projection at the base opposing end can be between 0.075 mm and 0.3 mm, inclusive.

In Example 10, the valve of any one or any combination of Examples 1-5 and 7-9, wherein the frustoconically shaped surface can extend between 20% and 100%, inclusive, of a total longitudinal length of the projection.

In Example 11, the valve of any one or any combination of Examples 1-10, wherein the apparatus can optionally further include: a mixing chamber configured to house a first component of the bone cement prior to mixing; and a connecting cylinder defining a conduit configured to fluidly connect the mixing chamber and the connecting cylinder; wherein the connecting cylinder can be configured to be selectively coupled to and removable from the mixing chamber, and wherein the valve can be configured to seal communication between the connecting cylinder when selectively coupled together and the valve and can be configured to seal the mixing chamber when the connecting is removed from the mixing chamber.

In Example 12, a valve for an apparatus configured to mix bone cement, the valve can optionally include: a base defining a first portion of a passage, the passage is configured to allow a component the bone cement through the valve; and a projection extending from the base to a base opposing end and forming a second portion of the passage that communicates with the first portion, wherein the projection is formed of elastomeric material having a shape memory configured to collapse the projection to seal the passage at the base opposing end of the projection, and wherein the projection has a frustoconically shaped inner surface that forms a part of the second portion of the passage.

In Example 13, the valve of Example 12, wherein the frustoconically shaped surface can optionally have an angle of between 5 degrees and 35 degrees, inclusive, relative to at least one of a longitudinal axis of the projection and a cylindrically shaped surface of the projection.

In Example 14, the valve of any one or any combination of Examples 12-13, wherein the projection can optionally have a first cylindrical portion forming the base opposing end of the projection.

In Example 15, the valve of any one or any combination of Examples 12-14, wherein the frustoconically shaped surface can extend between 20% and 100%, inclusive, of a total longitudinal length of the projection.

In Example 16, an apparatus for mixing bone cement, the apparatus can optionally include: a mixing chamber configured to house a first component of the bone cement prior to mixing; a connecting cylinder defining a conduit configured to fluidly connect the mixing chamber and the connecting cylinder; a cannula located within the connecting cylinder and in fluid communication with the conduit; a base including a pouch configured to house a second component of the bone cement, a portion of the base sized to be received within the connecting cylinder such that upon a relative movement between the base and the connecting cylinder, the pouch can be punctured by the cannula; a piston located within the mixing chamber and configured to engage the connecting cylinder; and a valve retained by the piston and configured to allow the second component of the bone cement to pass through the cannula from the pouch into the mixing chamber and collapse to seal the mixing chamber upon disengagement of the connecting cylinder from the piston, wherein the valve includes a projection extending from a base of the valve to a base opposing end thereof, the projection forming part of a passage that allows for passage of the second component through the valve when the valve is not in a collapsed state, and wherein the projection has a frustoconically shaped inner surface that forms a part of the passage.

In Example 17, the apparatus of Example 16, wherein the frustoconically shaped surface can optionally have an angle of between 5 degrees and 35 degrees, inclusive, relative to at least one of a longitudinal axis of the projection and a surface of a cylindrical portion of the projection.

In Example 18, the apparatus of any one or any combination of Examples 16-17, wherein the projection can optionally have a first cylindrical portion forming the base opposing end of the projection.

In Example 19, the apparatus of Example 18, wherein the first cylindrical portion can optionally have a longitudinal length of between 10% and 30%, inclusive, of a total longitudinal length of the projection.

In Example 20, the apparatus of any one or any combination of Examples 16-19, wherein the frustoconically shaped inner surface can extend between 20% and 100%, inclusive, of a total longitudinal length of the projection.

In Example 21, the apparatus of any one or any combination of Examples 16-20, wherein the projection can be formed of elastomeric material.

In Example 22, the apparatus of any one of or any combination of Examples 16-21, optionally further including a safety strip connected to the base, the safety strip configured to prevent the pouch from being punctured by the cannula until the safety strip is removed from the base.

In Example 23, the apparatus of any one of or any combination of Examples 16-22, optionally further including a filter connected to the piston and configured to prevent the first component from entering the valve assembly and the pouch upon puncturing of the pouch.

In Example 24, the apparatuses and valves of any one of or any combination of Examples 1-23 is optionally configured such that all elements or options recited are available to use or select from,

What is claimed is:

1. A valve for an apparatus configured to mix bone cement, the valve comprising:

a base defining a first portion of a passage, the passage is configured to allow a component of the bone cement through the valve; and a projection extending from the base to a base opposing end and forming a second portion of the passage that communicates with the first portion, the projection having a frustoconically shaped surface that comprises one of an outer surface or an inner surface that forms a part of the second portion of the passage, wherein the frustoconically shaped surface extends to an outer tip of the projection;

wherein the projection is formed of elastomeric material having a shape memory configured to collapse the projection to seal the passage at the base opposing end of the projection.

2. The valve of claim 1, wherein the frustoconically shaped surface has an angle of between 5 degrees and 35 degrees, inclusive, relative to a longitudinal axis of the projection.

3. The valve of claim 1, wherein the frustoconically shaped surface has an angle of between 5 degrees and 35 degrees, inclusive, relative to a cylindrically shaped surface of the proj ection.

4. The valve of claim 1, wherein the projection has a first cylindrical portion forming the base opposing end of the projection.

5. The valve of claim 4, wherein the first cylindrical portion has a longitudinal length of between 10% and 30%, inclusive, of a total longitudinal length of the projection.

6. The valve of claim 1, wherein the frustoconically shaped surface extends to the base opposing end of the projection.

7. The valve of claim 1, wherein the elastomeric material comprises silicone.

8. The valve of claim 1, wherein a thickness of a wall of the projection at the base opposing end is between 0.075 mm and 0.3 min, inclusive.

9. The valve of claim 1, wherein the frustoconically shaped surface extends between 20% and 100%, inclusive, of a total longitudinal length of the projection.

10. The valve of claim 1, wherein the apparatus further comprises:

a mixing chamber configured to house a first component of the bone cement prior to mixing; and a connecting cylinder defining a conduit configured to fluidly connect the mixing chamber and the connecting cylinder;

wherein the connecting cylinder is configured to be selectively coupled to and removable from the mixing chamber, and wherein the valve is configured to seal communication between the connecting cylinder when selectively coupled together and the valve and is configured to seal the mixing chamber when the connecting cylinder is removed from the mixing chamber.

11. A valve for an apparatus configured to mix bone cement, the valve comprising:

a base defining a first portion of a passage, the passage is configured to allow a component the bone cement through the valve; and a cylindrical projection extending from the base to a base opposing end and forming a second portion of the passage that communicates with the first portion, wherein the projection is formed of elastomeric material having a shape memory configured to collapse the projection to seal the passage at the base opposing end of the projection, and wherein the projection has a frustoconically shaped inner surface that forms a part of the second portion of the passage, wherein the frustoconically shaped inner surface extends to an outer tip of the projection.

12. The valve of claim 11, wherein the frustoconically shaped inner surface has an angle of between 5 degrees and 35 degrees, inclusive, relative to at least one of a longitudinal axis of the projection and a cylindrically shaped surface of the projection.

13. The valve of claim 11, wherein the projection has a first cylindrical portion forming the base opposing end of the projection.

14. The valve of claim 11, wherein the frustoconically shaped inner surface extends between 20% and 100%, inclusive, of a total longitudinal length of the projection.

15. A valve for an apparatus configured to mix bone cement, the valve comprising:

a base defining a first portion of a passage, the passage is configured to allow a component of the bone cement through the valve; and a projection extending from the base to a base opposing end and forming a second portion of the passage that communicates with the first portion, the projection having a frustoconically shaped surface that forms an inner surface of the projection, wherein the frustoconically shaped surface extends to an outer tip of the projection.

16. The valve of claim 15, wherein the frustoconically shaped surface has an angle of between 5 degrees and 35 degrees, inclusive, relative to a longitudinal axis of the projection.

17. The valve of claim 15, wherein the frustoconically shaped surface has an angle of between 5 degrees and 35 degrees, inclusive, relative to a cylindrically shaped surface of the projection.

18. The valve of claim 15, wherein the projection has a first cylindrical portion forming the base opposing end of the projection.

19. The valve of claim 18, wherein the first cylindrical portion has a longitudinal length of between 10% and 30%, inclusive, of a total longitudinal length of the projection.

20. The valve of claim 15, wherein the frustoconically shaped surface extends to the base opposing end of the projection.

21. The valve of claim 15, wherein the projection is formed of elastomeric material having a shape memory configured to collapse the projection to seal the passage at the base opposing end of the projection.

22. The valve of claim 21, wherein the elastomeric material comprises silicone.

* * * * *